(12) United States Patent
Wong et al.

(10) Patent No.: US 6,518,418 B1
(45) Date of Patent: Feb. 11, 2003

(54) NUCLEOTIDE SUGARS

(75) Inventors: Chi-Huey Wong, Rancho Santa Fe, CA (US); Hirosato Kondo, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 07/991,182

(22) Filed: Dec. 10, 1992

Related U.S. Application Data

(63) Continuation-in-part of application No. 07/961,076, filed on Oct. 14, 1992, now Pat. No. 6,319,695, which is a continuation-in-part of application No. 07/910,612, filed on Jul. 8, 1992, now abandoned, which is a continuation-in-part of application No. 07/901,260, filed on Jun. 19, 1992, now abandoned, which is a continuation-in-part of application No. 07/777,662, filed on Oct. 15, 1991, now abandoned.

(51) Int. Cl.[7] .............................................. C07H 21/00
(52) U.S. Cl. ................ 536/25.34; 536/18.6; 536/26.23; 536/26.41; 536/26.5; 536/26.8
(58) Field of Search ........................ 536/26.23, 6, 18.6, 536/26.8, 55.2, 123, 26.41, 26.5

(56) References Cited

U.S. PATENT DOCUMENTS

| | | | |
|---|---|---|---|
| 4,704,361 A | * 11/1987 | Miccoli et al. | 536/26.41 |
| 4,925,796 A | 5/1990 | Bergh et al. | 435/97 |
| 4,973,679 A | * 11/1990 | Caruthers et al. | 536/26.72 |
| 5,109,126 A | 4/1992 | Agrawal et al. | 536/26.23 |
| 5,220,008 A | 6/1993 | Sabesan et al. | 536/4.1 |
| 5,352,670 A | 10/1994 | Venot et al. | 514/54 |

FOREIGN PATENT DOCUMENTS

DE 3626915 * 11/1988

OTHER PUBLICATIONS

J. Org. Chem. 55 (16) (1990). Heckes.*

J. Org. Chem. 57 (10) (1992) gchikawa.*

White et al Principles of Biochemistry. Fifth Edition. McGraw–Hill, New York: 1973, pp. 466 and 486–488.*

* cited by examiner

*Primary Examiner*—Howard V. Owens
(74) *Attorney, Agent, or Firm*—Donald G. Lewis; Thomas Fitting

(57) ABSTRACT

Phosphite linked nucleotide sugars, e.g. nucleoside-monophosphite-glycosides, are synthesized using phosphoramiditing agents. The success of the synthetic method is largely independent of the choice of sugar and of nucleotide. The phosphite linked nucleotide sugars are shown to be useful, in the presence of an oxidizing agent, for the production of phosphate linked nucleotide sugars, e.g. nucleoside-monophosphate-glycosides.

11 Claims, 2 Drawing Sheets

NUCLEOTIDE SUGARS

CROSS-REFERENCE TO RELATED APPLICATIONS

The present application is a continuation-in-part of U.S. patent application Ser. No. 07/961,076, filed Oct. 14, 1992, now U.S. Pat. No. 6,319,695, that is a continuation-in-part of U.S. patent application Ser. No. 07/910,612, filed Jul. 8, 1992, now abandoned, that is a continuation-in-part of U.S. patent application Ser. No. 07/901,260, filed Jun. 19, 1992, now abandoned, that is a continuation-in-part of U.S. patent application Ser. No. 07/777,662, filed Oct. 15, 1991, now abandoned, whose disclosures are incorporated herein by reference.

GOVERNMENT RIGHTS

This invention was made with government support under Grant No. GM 44154 awarded by the National Institutes of Health. The U.S. government has certain rights in the invention.

FIELD OF THE INVENTION

The invention relates to a synthesis of phosphite linked nucleotide sugars, e.g. nucleoside-monophosphite-glycosides, and to the use of such phosphite compounds in the presence of an oxidizing agents to produce phosphate linked nucleotide sugars, e.g. nucleoside-monophosphate-glycosides. More particularly, the invention relates to the use of phosphoramiditing agents for synthesizing phosphite linked nucleotide sugars and to the use of such phosphite linked nucleotide sugars, in the presence of an oxidant, for producing phosphate linked nucleotide sugars.

BACKGROUND OF THE INVENTION

Several phosphate linked nucleotide sugars may be enzymatically synthesized using well characterized metabolic pathways. One example of such a metabolic pathway involves the synthesis of β-sialyl CMP. However, some of these metabolic pathways, as for instance the β-sialyl CMP pathway, are highly substrate specific, i.e. only a very narrow range of substrate analogs may be substituted within the pathway.

Phosphate linked nucleotide sugars have many uses. In one important application, nucleotide sugars are employed as substrates for elongating oligosaccharides.

The elongation of oligosaccharides can be achieved by means of metabolic pathways which employ a transferase. The transferase catalyzes the glycosidic transfer of a sugar from a nucleotide sugar to an oligosaccharide. The first half of the transfer reaction involves the hydrolytic cleavage of the nucleotide sugar at the glycosidic bond between the sugar to the phosphate group attached to the nucleotide. The second half of the transfer reaction involves the formation of a new glycosidic bond between the sugar donor and the oligosaccharide acceptor.

Examples of transfer reactions include fucosyl transferase which employs GDP-fucose to elongate lactose and sialyl transferase which employs CMP-sialic Acid to elongate lactose.

In some instances, the substrate specificity of the glycosyl transferase reaction is relatively lax with respect to the sugar portion of the nucleotide sugar. Accordingly, a relatively wide range of sugar analogs may be employed to elongate the oligosaccharide acceptors.

The desirability of incorporating a sugar analog into at least one oligosaccharide is disclosed herein. Incorporation of unnatural or sialidase-resistant sialic acid analogs into sialyl Lewis$^x$ and other glycoconjugates can serve to enhance the half life of such compositions.

Unfortunately, as indicated above, several metabolic pathways for the production of phosphate linked nucleotide sugars are substrate specific, including the metabolic pathway for production of β-sialyl CMP. It is disclosed herein that it would be useful to develop an alternative synthetic pathway for the synthesis of phosphate linked nucleotide sugar analogs so that such sugar analogs may be incorporated by elongation into various oligosaccharides.

The chemical synthesis of β-sialyl CMP and similar phosphate linked nucleotide sugar is made difficult by its tertially hindered anomeric center and the lack of an electron-demanding group (e.g. OH or AcNH) adjacent to the anomeric center of the sialic acid. What was needed was a facile non-enzymic method for producing a wide range of phosphate linked nucleotide sugars using a variety of sugars and sugar analogs.

Phosphoramiditing agents are employed in the prior art for synthesizing non-glycosidically linked phosphite nucleotide sugars, e.g. 3'nucleoside-monophosphite-5'ribose. (e.g. Beaucage et al., U.S. Pat. No. 4,973,679). Phosphoramiditing agents are also employed in the prior art for synthesizing glycosidically linked sugar phosphite alcohols, e.g. N-acetyl-D-glucosamine-glycerate ether. (Hecker et al., Journal of Organic Chemistry (1990), vol. 55 (16), 4904–4911). However, there is no teaching in the prior art for making glycosidically linked phosphite nucleotide sugars.

What was needed was a synthetic method employing phosphoramiditing agents for producing glycosidically linked phosphite nucleotide sugars and a showing that such glycosidically linked phosphite nucleotide sugars could be easily converted to the corresponding phosphate linked nucleotide sugar in the presence of an oxidizing agent.

SUMMARY

Protected sugars having an unprotected glycosidic oxygen are reacted with a phosphoramiditing agent to form the corresponding glycosidically linked phosphoramidite sugar (protected). The glycosidically linked phosphoramidite sugar is then reacted with a protected nucleoside to produce the corresponding glycosidically linked phosphite nucleotide sugar (protected). In the presence of an oxidant, glycosidically linked phosphite nucleotide sugar may be converted to the corresponding glycosidically linked phosphate nucleotide sugar (protected). The resultant glycosidically linked phosphate nucleotide sugar may then be de-protected to produce a product employable with a glycosyl transferase for the elongation of oligosaccharides. The above synthesis of nucleotide sugars is non-specific with respect to the sugar substrate. However, the sugar substrates must have protected side groups and a free glycosyl group.

BRIEF DESCRIPTION OF THE DRAWING

FIG. 1 illustrates methyl 5-acetamido-3,5,-dideoxy-β-D-glycero-D-galacto-2-nonulopyranosonic acid, i.e. sialic acid.

FIG. 2 illustrates the sialic acid of FIG. 1 protected by acetylation, i.e. methyl 5-acetamido-4,7,8,9-tetra-O-acetyl- 3,5,-dideoxy-β-D-glycero-D-galacto-2-nonulopyranosonate.

FIG. 3 illustrates a phosphoramidited form of the protected sialic acid of FIG. 2.

FIG. 4 illustrates a protected cytidine, i.e. 4-N-benxoyl-2',3'-di-O-benzoyl-cytidine.

FIG. 5 illustrates a protected glycosidically linked phosphite-cytidine-sialic acid produced by linking the protected cytidine of FIG. 4 to the protected phorphoramidited sialic acid of FIG. 3.

DETAILED DESCRIPTION OF THE INVENTION

Phosphite Linked Nucleotide Sugars:

One of the preferred phosphite linked nucleotides is a protected nucleoside monophosphite-glycoside, e.g. protected β-sialyl CMP (5). The protected nucleoside monophosphite-glycoside comprises a protected glycosidic sugar, a protected nucleoside, and a protected monophosphite linkage group.

Figure 1:
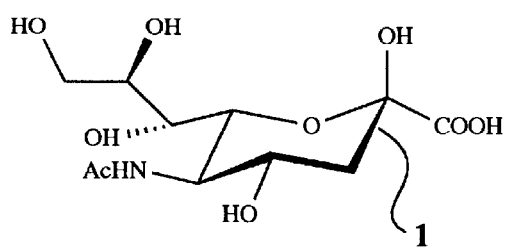
FIGS. 1–5 illustrate a series of compounds leading to the synthesis of 5'cytidine-phosphite-2'sialic acid and for the oxidation of such phosphite compound to produce the corresponding phosphate linked CMP-sialic acid.
Figure 2:
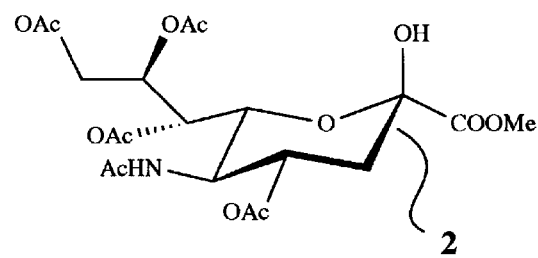
Figure 3:
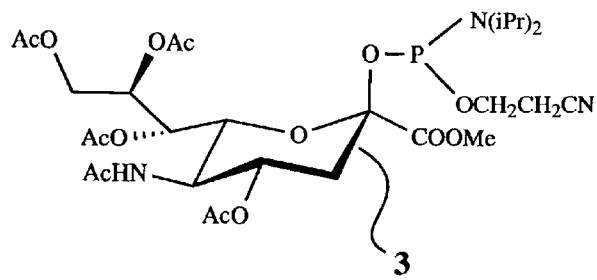

An example of a protected sugar employable as a precursor for the protected glycoside is illustrated in FIG. 2, i.e. acetylated sialic acid (2). The precursor sugar 2 has an unprotected anomeric carbon but otherwise has side groups which are protected or unreactive. Acetylation is a preferred method for protecting hydroxyl and amino side groups. Methylation is a preferred method for protecting acid groups. Other side groups may be protected according to methods known in the prior art. A preferred protected glycoside includes sialic acid 2 protected by acetylation at positions 4,7,8, and 9 and by methylation of the acid group at position 1, the glycosyl oxygen occupying position 2. Fucose is also a preferred sugar to employ as a precursor of a protected glycoside.

Figure 4:
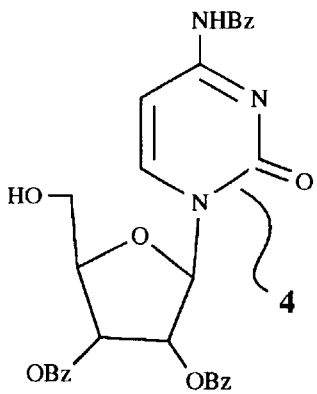
Figure 5:
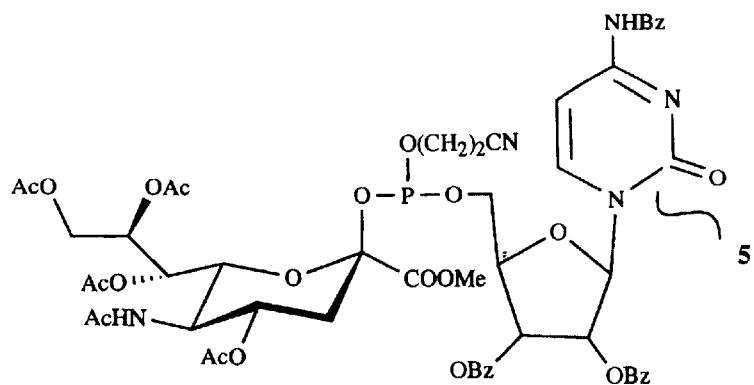
Figure 6:
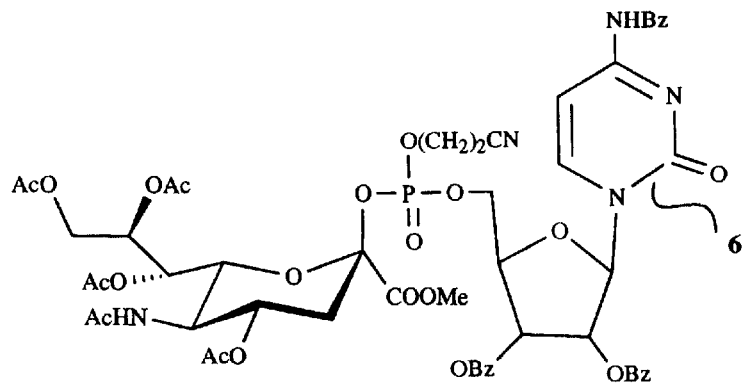
FIG. 6 illustrates a protected glycosidically linked phosphate-cytidine-sialic acid produced by oxidizing the composition of FIG. 5.
Figure 7:
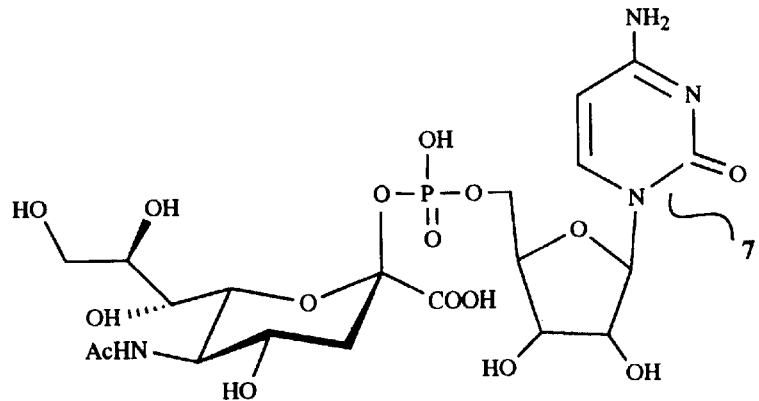
FIG. 7 illustrates β-sialyl-CMP produced by deprotecting the composition of FIG. 6.

A precursor of the protected nucleoside comprises a protected ribose sugar glycosidically linked to a protected nucleic acid. A preferred protected nucleoside 4 is illustrated in FIG. 4. Benzoylation is a preferred method for protecting ribose and nucleic acid side groups. The protected ribose includes one unprotected hydroxyl group for forming a phosphite linkage. The preferred position for the unprotected hydroxyl group is in the 5' position of the ribose. Preferred nucleosides include adenosine, cytidine, guanosine, uridine, and inosine. A preferred protected cytidine is protected with benzoyl groups positioned in the N-4, 2', and 3' positions.

The protected monophosphite linkage group links the anomeric carbon of the protected sugar with the unprotected hydroxyl oxygen on the ribose of said nucleoside. A preferred monophosphite linkage group includes a protective o-cyanoethyl group.

Another preferred composition is a protected nucleoside phosphate-phosphite-glycoside. This composition comprises a protected glycoside having an anomeric carbon, a protected nucleoside monophosphate having a ribose with a phosphate group, and a protected monophosphite linkage group linking the anomeric carbon of the protected glycoside with the phosphate group on the ribose of the nucleoside.

A Method for Synthesizing Phosphite Linked Nucleotide Sugars

A preferred protocol for synthesizing protected nucleoside monophosphite-glycosides includes the following steps, viz.:

1. Providing a sugar having an unprotected anomeric carbon and protected or unreactive side groups on other carbon atoms. Preferred sugars include sialic acid and fucose.
2. Providing a phosphoramiditing agent. Preferred phosphoramiditing agent include 2-cyanoethyl-N,N-diisopropylchlorophosphoramidite and methyl-N,N-diisopropylphosphoramidite.
3. Providing a protected nucleoside having an unprotected ribose hydroxyl oxygen, preferably in the 5' position. Preferred protected nucleosides include adenosine, cytidine, guanosine, uridine, and inosine.
4. Forming a sugar phoshporamidite 3 by reacting the sugar of the first step with the phosphoramiditing agent of the second step under nonreducing conditions for forming a glycosidic bond between the anomeric carbon of the sugar of the first step and the phosphoramiditing agent of the second step; and then
5. Reacting the sugar phosphoramidite of step 4 with the nucleoside of step 3 under nonreducing conditions for forming the protected nucleoside monophosphite-glycoside.

Example I

A protected β-sialyl monophosphite cytidine may be synthesized according to the following method, viz.:

Provision of Protected Sialic Acid:

Methyl 5-acetamido-4,7,8,9-tetra-O-acetyl-3,5-dideoxy-β-D-glycero-D-galacto-2-nonulopyranosonate (2a) was prepared by the procedure of Marra and Sinay.[1] Alternatively, a mixture of methyl 2-chloro-5-acetamido-4,7,8,9-tetra-O-acetyl-3,5-dideoxy-β-glycero-D-galacto-2-nonulopyranosonate[2] (0.67 g, 1.3 mmol) and silver carbonate (0.363 g, 1.3 mmol) in acetone (5 mL) - $H_2O$ (0.5 mL) was stirred for 10 h at room temperature. The suspension was filtered by passing through a Celite 545 bed and the filtrate was evaporated to dryness and the residue was diluted with chloroform, washed with water and brine, and then dried over sodium sulfate. The solution was evaporated in vacuo to give a crude material, which was chromatographed on a silica gel column (chloroform - methanol 25:1) to give 2a (0.568 g, 88%) as a white needles.

$^1$H-NMR ($CDCl_3$) δ 1.90, 2.02, 2.03, 2.10, 2.14 (3H each, s, 4xOAc and NAc), 2.17 (1H, dd, J 5.04, 12.72 Hz, H-3eq), 2.29 (1H, dd, J 11.52, 12.72 Hz, H-3ax), 3.87 (3H, s, COOMe), 4.02 (1H, dd, J 7.04, 12.4 Hz, H-9), 4.12 (1H, dd, J 2.1,7.8 Hz, H-6), 4.13 (1H, d, J 7.8 Hz, NH), 4.17 (1H, ddd, 7.8, 9.8, 10.28, Hz, H-5), 4.42 (1H, dd, J 1.92, 12.4 Hz, H-9'), 5.20–5.26 (2H, m, H-4 and H-8), 5.32 (1H, dd, J 2.1, 6.50 Hz, H-7), 5.37 (1H. bs. OH).

Provision of protected CMP:

4-N-Benzoyl-2',3'-di-O-benzoyl-cytidine (7)

To a solution of N-4-benzoyl cytidine (2.2 g, 6.34 mmol) in pyridine (55 mL) was added t-butyldimethylsilyl chloride (1.24 g, 8.24 mmol) dropwise and the reaction mixture was stirred for 2 days. To the mixture was added benzoic anhydride (2.26 g, 10 mmol) and the mixture was stirred for 5 h at room temperature. The mixture was then poured onto ice-water and extracted with AcOEt. The organic layer was washed with ice-coled 5% HCl, saturated aqueous $NaHCO_3$ and dried over sodium sulfate and concentrated. The residue was chromatographed on a silica gel column ($CHCl_3$—$CH_3OH$, 25:1) to give 4-N-benzoyl-2'3'-di-O-benzoyl-5'-O-t-butyldimethylsilyl cytidine (1.2 g) as white powder.

$^1$H-NMR ($CDCl_3$) δ 0.22, 0.23 (3H each, s, $CH_3$ of TBDMS), 1.02 (9H, s, t-Bu), 4.03 (1H, dd, J 1.6, 11.6 Hz, H-5a'), 4.10 (1H, dd, J 1.6, 11.6 Hz, H-5b'), 4.51 (1H, d, J 2.4, H-4'), 5.65 (1H, dd, J 5.6, 6.4 Hz, H-2'), 5.78 (1H, dd, J 2A, 5.2 Hz, H-3'), 6.79 (1H, d, J 6.4 Hz, H-1'). HRMS calcd for $C_{36}H_{39}N_3O_8SiCs$ (M+Cs$^+$) 802.1561, found 802.1561.

To a solution of the above obtained 4-N-benzoyl-2',3'-di-O-benzoyl-5'-O-t-butyldimethylsilyl cytidine (0.38 g, 0.57 mmol) in $CH_3CN$—$H_2O$ (20 mL-1mL) was added tetrabutylammonium flouride (1.4 mL) and the reaction mixture was stirred for 24 h at room temperature. The mixture was evaporated in vacuo to give a crude material which was chromatographed on a silica gel column (AcOEt-hexane, 1:1) to give 7 (0.2 g, 63%) as white powder.

$^1$H-NMR ($CDCl_3$) δ 4.02 (1H, dd, J 4.4, 12.4 Hz, H-5a'), 4.14 (1H, bd, J 12.4 Hz, H-5b'), 4.52 (1H, dd, J 2.4, 4.4 Hz, H-4'), 5.91 (1H, dd, J 4.8, 5.6 Hz, H-2'), 5.98 (1H t, J 5.6 Hz, H-3'), 6.34 (1H, d, J 4.8 Hz, H-1'). HRMS calcd for $C_{30}H_{25}N_3O_8Cs$ (M+Cs$^+$) 688.0696, found 688.0698.

Formation of β-sialyl Phosphoramidite:

To a solution of 2-cyanoethyl N,N-diisopropylchlorophosphoramidite (0.29 g, 1.22 mmol) and iPr$_2$NEt (0.53 g, 4.1 mmol) in dry $CH_2Cl_2$ (20 mL) under argon atmosphere, was added 2a (0.4 g, 0.81 mmol) at 0° C. After 3 h at 20° C., the reaction solution was diluted with $CH_2Cl_2$ (20 mL) and washed with ice-cold aqueous $NaHCO_3$, saturated NaCl, and water. The organic layer was dried with $Na_2SO_4$ and filtrate was concentrated to afford crude 6 as pale brown syrup. Crude 6 was chromatographed on silica gel (EtOAc) to provide 6 (0.5 g, 89%) as a colorless syrup. HRMS: calcd for $C_{29}H_{46}N_3O_{14}PCs$ (M+Cs$^+$) 824.1772, found 824.1780. Compound 9 was prepared according to the procedure described previously.[4]

Formation of β-sialyl Phosphite Cytidine:

To a stirred solution of $CH_3CN$ under argon atmosphere at 5° C. containing 0.029 millimolar of the protected cytidine and 0.029 millimolar of 1H-tetrazole is added 0.003 millimolar of the β-sialyl-phorphoramidite. The above mixture is then allowed to warm up to room temperature and stirred for 5 hours at that temperature. The resultant β-sialyl phosphite cytidine is then extracted and dried under nonreducing conditions from the above room temperature mixture.

Method of Synthesizing Phosphate Linked Nucleotide Sugars

Protected phosphate linked nucleotide sugars may be easily obtained by oxidation of the correspondinig protected phosphite linked nucleotide sugar.

Example II

Protected β-sialyl CMP may be synthesized according to the following method, viz.:

Protected β-sialyl monophosphite cytidine is obtained as indicated in Example II. The protected β-sialyl monophosphite cytidine is then oxidized to obtain the corresponding protected β-sialyl CMP. To a dry $CH_3CN$ solution containing protected β-sialyl monophosphite cytidine is added an excess of t-BuO$_2$H at −30° C. Then the above mixture is allowed to warm up to room temperature and stirred for 30 minutes. The reaction in the above room temperature mixture is then stopped by the addition of $CHCl_3$ and washed with ice-cold $NaHCO_3$ to form an organic layer. The organic layer of the stopped mixture is then dried over anhydrous sodium sulfate and evaporated in vacuo to give the protected nucleoside monophosphate-glycoside, i.e. the protected β-sialyl CMP.

Method for Synthesizing Nucleoside Phosphate-Phosphite Glycoside

The synthesis of a nucleoside phosphate-phosphite glycoside is similar to the synthesis of the nucleoside phosphite glycoside, as indicated above. However, in the synthesis of the former composition, a protected nucleotide is provided in the third step in place of the protected nucleoside, accordingly to established procedures. This protected nucleotide is then reacted with the desired sugar phosphoramidite under nonreducing conditions for forming the protected nucleoside phosphate-phosphite-glycoside.

Method for Synthesizing Diphosphate Linked Nucleotide Sugars

A protected nucleoside diphosphate-glycoside may be easily synthesized by oxidation of the correponding protected nucleoside phosphate-phosphite-glycoside under substantially identical conditions as described for the oxidation of protected nucleoside phosphite-glycoside to form protected nucleotide sugars.

What is claimed is:

1. A process for preparing a protected nucleoside monophosphite-glycoside comprising the following steps:

Step A: providing a sugar having an unprotected anomeric carbon but otherwise having protected side groups;

Step B: providing a phosphoramiditing agent;

Step C: providing a nucleoside having an unprotected ribose hydroxyl oxygen but otherwise having protected side groups; then Step D: forming a sugar phosphoramidite by reacting the sugar of said Step A with the phosphoramiditing agent of said Step B under for forming a glycosidic bond between the anomeric carbon of the sugar of said Step A and the phosphoramiditing agent of said Step B; and then Step E: reacting the sugar phosphoramidite of said Step D with the nucleoside of said Step C for forming the protected nucleoside monophosphite-glycoside, wherein:

the protected side groups of said Step A being protective against reactivity in said Step D with the phosphoramiditing agent of said Step B.

2. A process for preparing a protected nucleoside monophosphite-glycoside as in claim 1 wherein:

in said Step B: the phosphoramiditing agent is selected from the group consisting of 2-cyanoethyl-N,N-diisopropylchlorophosphoramidite and methyl-N,N-diisopropylphosphoramidite.

3. A process for preparing a protected nucleoside monophosphite-glycoside as in claim 1 wherein:

in said Step A: the sugar is selected from the group consisting of sialic acid and fucose.

4. A process for preparing a protected nucleoside monophosphite-glycoside as in claim 1 wherein:

in said Step C: the nucleoside is selected from the group consisting of adenosine, cytidine, guanosine, uridine, and inosine.

5. A process for preparing a protected nucleoside monophosphite-glycoside as in claim 4 wherein:

the unprotected hydroxyl oxygen on the ribose of said nucleoside occupies a 5' position.

6. A process for preparing a protected nucleoside monophsphite-glycoside as in claim 4 wherein:

said nucleoside is cytidine and said cytidine is protected with benzoyl groups positioned in the N-4, 2', and 3' positions.

7. A process for preparing a protected nucleoside monophosphite-glycoside as in claim 1 wherein said Step D for forming the phorphoramidite glycosidically linked to the protected glycoside includes the following Substeps:

Substep D.1: a solution of dry $CH_2Cl_2$ containing 1.22 millimolar 2-cyanoethyl-N,N-diisopropylchlorophosphoramidite and 4.1 millimolar $iPr_2NEt$ is made 4.1 millimolar by the addition of the sugar of said Step A, the addition occurring at 0° C. under an argon atmosphere; then Substep D.2: the solution of said Substep d.1 is allowed to react for 3 hours at 20° C.; and then Substep D.3: the reaction of said Substep D.2 is stopped by dilution with an equal volume of $CH_2Cl_2$ and washing with ice-cold aqueous $NaHCO_3$, saturated with NaCl, and then water to form an organic layer; and then Substep D.4: the organic layer of said Substep D.3 is dried with $Na_2SO_4$ and a filtrate is concentrated to yield the glycosidically linked sugar phorphoramidite.

8. A process for preparing a protected nucleoside monophosphite-glycoside as in claim 7 wherein said Step E for forming the protected nucleoside monophosphite-glycoside includes the following Substeps:

Substep E.1: to a stirred solution of $CH_3CN$ under argon atmosphere at 5° C. containing 0.029 millimolar of the protected nucleoside of said Step C and 0.029 millimolar of 1H-tetrazole is added 0.003 millimolar of the sugar phorphoramidite of said Step D; then Substep E.2: the mixture of said Substep E.1 is allowed to warm up to room temperature and stirred for 5 hours at that temperature; and then Substep E.3: the nucleoside monophosphite-glycoside is then extracted and dried under nonreducing conditions from the mixture of said Substep E.2.

9. A process for preparing a protected nucleoside monophosphate-glycoside comprising the following steps:

Step A: providing a sugar having an unprotected anomeric carbon but otherwise having protected side groups;

Step B: providing a phosphoramiditing agent;

Step C: providing a nucleoside having an unprotected ribose hydroxyl oxygen but otherwise having protected side groups; then Step D: forming a sugar phoshporamidite by reacting the sugar of said Step A with the phosphoramiditing agent of said Step B under nonreducing conditions for forming a glycosidic bond between the anomeric carbon of the sugar of said Step A and the phosphoramiditing agent of said Step B; then Step E: reacting the sugar phosphoramidite of said Step D with the nucleoside of said Step C under nonreducing conditions for forming the protected nucleoside monophosphite-glycoside; and then Step F: oxidizing the protected nucleoside monophosphite-glycoside of said Step E to form the protected nucleoside monophosphate-glycoside.

10. A process for preparing a protected nucleoside monophosphate-glycoside as in claim 9 wherein said Step F for oxidizing the protected nucleoside monophosphite-glycoside of said Step E to form the protected nucleoside monophosphite-glycoside of said Step includes the following Substeps:

Substep F.1: to a dry $CH_3CN$ solution containing the protected nucleoside monophosphite-glycoside of said Step E is added an excess of $t-BuO_2H$ at −30° C.; then Substep F.2: the mixture of said Substep F.1 is then allowed to warm up to room temperature and stirred for 30 minutes; then Substep F.3: the reaction of said Substep F.2 is stopped by the addition of $CHCl_3$ and washed with ice-cold $NaHCO_3$ to form an organic layer; and then Substep F.4: the organic layer of said Substep F.3 is then dried over anhydrous sodium sulfate and evaporated in vacuo to give the protected nucleoside monophosphate-glycoside.

11. A process for preparing a protected nucleoside diphosphate-glycoside comprising the following steps:

Step A: providing a sugar having an unprotected anomeric carbon but otherwise having protected side groups;

Step B: providing a phosphoramiditing agent;

Step C: providing a nucleoside monophosphate having an unprotected ribose hydroxyl oxygen but otherwise having protected side groups; then Step D: forming a sugar phoshporamidite by reacting the sugar of said Step A with the phosphoramiditing agent of said Step B under nonreducing conditions for forming a glycosidic bond between the anomeric carbon of the sugar of said Step A and the phosphoramiditing agent of said Step B; and then Step E: reacting the sugar phosphoramidite of said Step D with the nucleoside monophosphate of said Step C under nonreducing conditions for forming the protected nucleoside monophosphite-phosphate-glycoside.

* * * * *